United States Patent
Scholl

[19]

[11] Patent Number: 6,030,201
[45] Date of Patent: Feb. 29, 2000

[54] PROCESS AND DEVICE FOR PRODUCING A PROPHYLACTIC

[76] Inventor: Thomas Scholl, 14, Quai Kleber, F-67000 Strassbourg, France

[21] Appl. No.: 08/716,442

[22] PCT Filed: Mar. 18, 1995

[86] PCT No.: PCT/DE95/00374

§ 371 Date: Nov. 27, 1996

§ 102(e) Date: Nov. 27, 1996

[87] PCT Pub. No.: WO95/25622

PCT Pub. Date: Sep. 28, 1995

[30] Foreign Application Priority Data

Mar. 19, 1994 [DE] Germany ............................ 44 09 449
Sep. 28, 1994 [DE] Germany ............................ 44 34 701

[51] Int. Cl.[7] ................................ B28B 7/04; B28B 1/38
[52] U.S. Cl. ................. 425/274; 425/275; 425/436 RM; 264/39; 264/301; 264/303; 264/304; 264/305
[58] Field of Search .......................... 264/39, 301, 303, 264/305, 334, 335, 304; 425/270, 269, 272, 274, 275, 273, 404, 436 RM

[56] References Cited

U.S. PATENT DOCUMENTS 1,923,733   8/1933   Killian ................................. 425/174
2,021,299  11/1935   Gammeter .......................... 264/301
5,323,544   6/1994   Osgood ................................ 34/247

FOREIGN PATENT DOCUMENTS 1566365    9/1967   Germany.
1616474    4/1971   Germany.
4130220   12/1992   Germany.
 429147    6/1967   Switzerland.
1142443    2/1969   United Kingdom.
WO 94/13231 6/1994   WIPO.

Primary Examiner—Catherine Timm
Assistant Examiner—Suzanne E. Mason
Attorney, Agent, or Firm—Collard & Roe, P.C.

[57] ABSTRACT

A process and a device for producing a thin-walled prophylactic, which is manufactured in a plurality of immersion stages, is disclosed. The device includes an endless conveyer belt on which an elongated cylindrical immersion tool is mounted. The process substantially consists of three immersion stages and three different immersion tubs, whereby the depths of immersion of the immersion tools substantially deviate from each other. After each immersion stage, a predetermined heat treatment of the elastic material applied to the immersion tool is carried out.

12 Claims, 5 Drawing Sheets

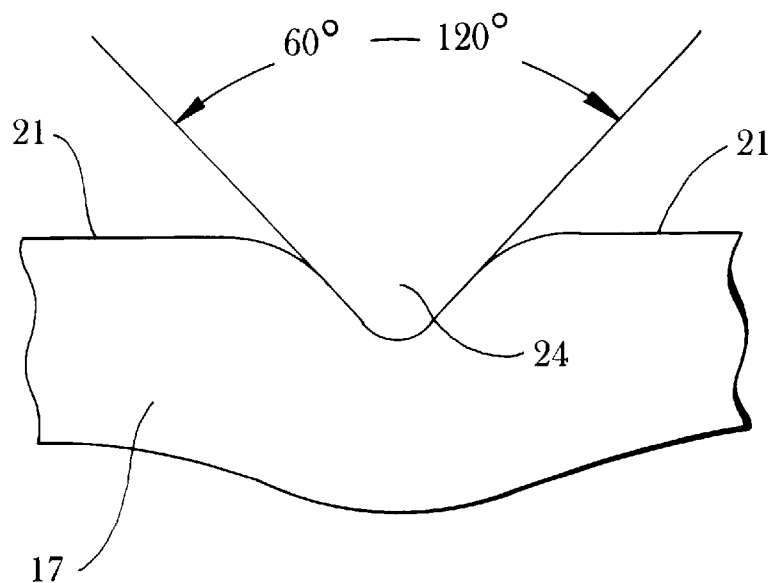
Fig. 3
Fig. 4
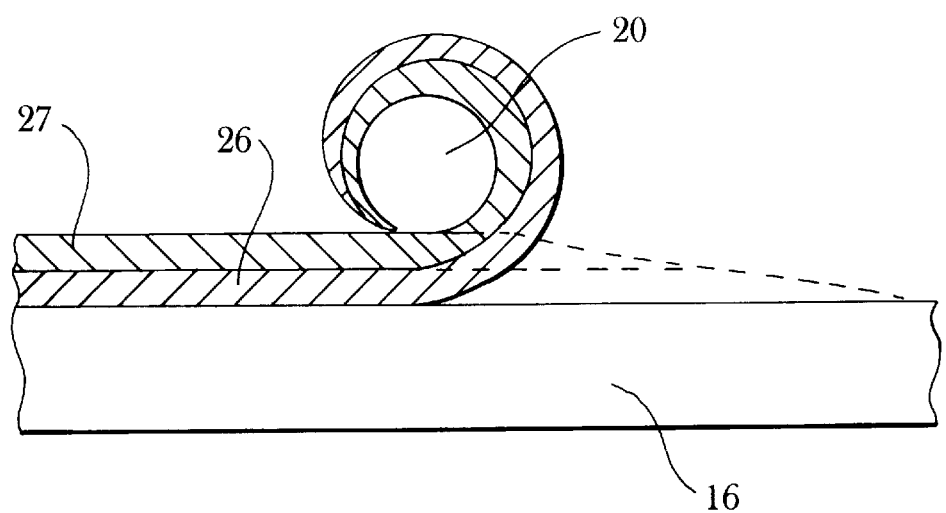

PROCESS AND DEVICE FOR PRODUCING A PROPHYLACTIC

The invention relates to a process and a device for producing a prophylactic from thin-walled elastic material (latex). In particular, the invention deals with a possible device for producing the prophylactic according to the process defined according to claim 1.

Such processes and devices for producing thin-walled molded bodies particularly from natural rubber compounds are known in the state of the art. In connection with the known processes for producing a prophylactic, usually one or two immersion stages are involved, whereby the immersion tool, which, as a rule, can be manufactured from polished metal, porcelain, wood or glass, is slowly immersed with its total immersion length in an immersion tub filled with a latex mixture, and slowly pulled out again. A drying stage takes place between the first immersion stage and the second immersion stage in that the water present on the immersion tool and on the applied elastic material is removed by evaporation.

Without entering into each individual process step of the known process, it is impossible with such a process to produce from one and the same elastic material a prophylactic with an elastic ring according to the invention that satisfies the requirements specified by the health authorities with respect to a prophylactic for preventing conception or for protection against infectious diseases.

With the processes and devices known in the state of the art, it is possible to produce multiple rings enclosing the top part of the prophylactic; however, not an individual ring having multiple times the mass of the rings known in the state of the art.

Another form of a prophylactic known in the state of the art is described in published document UK-1,142,443. This is a prophylactic having in the upper closed part a certain contour in the longitudinal cross section, which contour is adapted to the anatomical form of the male member. The drawback with said anatomical form is the fact that even though the anatomical form is given, no point of support is present along the inside wall of the prophylactic that provides the latter with a safe and comfortable support.

Furthermore, with the immersion production processes known in the state of the art, it is impossible to produce a multicolored prophylactic to which the color does not have to be applied to the outer surface of the prophylactic in a later work step, which finally represents an annoying factor when it is used.

Therefore, the problem of the present invention is to make available a prophylactic which, in the front part, has a ring made of elastic material, and which, if need be, can be produced multicolored, whereby the prophylactic is flawless in the material and conforming to the requirements of the testing authorities.

According to the invention, said problem is solved by the characterizing features contained in the main claims.

According to the introductory part of the process according to the invention, said process is characterized in that the immersion tool, with more than one immersion stage, is immersed in the liquid elastic material to be applied with different depths, whereby it is decisively important that the first immersion depth is substantially shorter than the subsequent immersion depths, and that after each immersion stage, a heat treatment of the immersion tool with the applied elastic material (latex) takes place.

The device according to the invention, such device belonging to the process of the invention for producing a prophylactic, is substantially characterized in that it has three immersion tubs, in which a special mixture (latex) substantially consisting of natural rubber is present, whereby the first of the three immersion tubs is, relative to the endless conveyor belt, disposed substantially lower than the two other immersion tubs, and provision is made for drying furnaces, such a furnace being arranged between the first and the second immersion tub and between the second and the third immersion tub, such furnaces being assigned a certain temperature profile and temperature program, in which the maximum temperature comes to about 70° C.; and provision is made after the third immersion tub first for a drying furnace, a brush device and a further drying furnace; and said device having a furnace extending over the entire length of the endless conveyor belt, said furnace being assigned a certain temperature profile and temperature program, whereby the maximum temperature does not exceed about 110° C.

Particularly important in connection with the present invention is the quality of the immersion tool according to the invention, which preferably is a glass cylinder, which is closed at one end. Within the zone of the closed end, the immersion tool has in an advantageous way a certain contour with a deepening (ditch) which at the deepest point, may have an annular groove according to the invention, the opening angle of such groove varying between 60° and 120°. When planning the measurements for the annular groove it is advantageous to select the depth of the annular groove between 0.3 and 1.5 mm. In addition to various embodiments of the immersion tool according to the invention, the embodiment seems to be most advantageous in which two truncated cone-like sections having their jacket surfaces designed in a slightly spherical way adjoin the annular groove laterally.

A particularly advantageous reservoir part according to the invention is present at the top, closed end of the glass immersion tool, said part being designed in the way of a club, whereby the thinner end of the club adjoins the glass piston, and the top, larger end of the club forms the termination of the reservoir part. The advantageous measurements for the reservoir part are about 12 mm in the top, wider part of the club, and 4 to 10 mm in the lower, narrower part of the reservoir, whereby the length of the reservoir part amounts to about 16 mm.

Additional features essential to the invention are contained in the dependent claims.

The invention is now described in greater detail in the following by reference to the drawings, in which:

FIG. 3 shows a cut part view of the deepening with the annular groove (24) according to the invention;

FIG. 4 shows a part view of the immersion tool (14) with a shaped rolling ring (20) at the end of the immersion layers;

Figure 1:
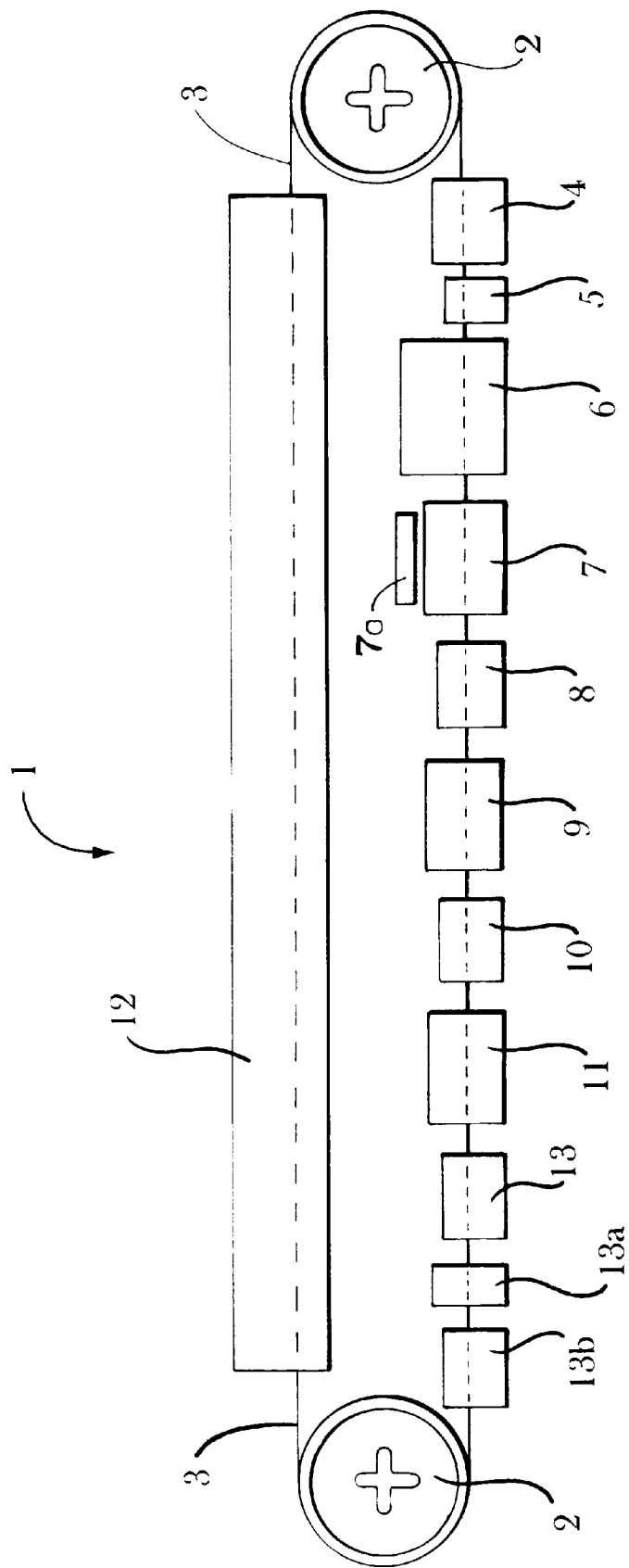
FIG. 1 shows a schematic representation of the device (1) operating according to the process of the invention.

FIG. 1 shows a schematic representation of the device according to the invention for producing a thin-walled prophylactic, which is manufactured in a number of immersion stages. The device 1 consists of an endless conveyor belt 3, which is guided across the two rollers 2 and driven by the latter with the required conveying speed. The immersion tools according to the invention, which are not shown in this drawing but described in greater detail below, are mounted on the endless conveyor belt 3.

The important process steps of the process of the invention, or manufacturing process, are described in detail in the following.

The immersion tools with the almost finished prophylactics, said tools being mounted on the endless conveyor belt 3, are received via the rollers 2 in a washing basin 4, which has the important function of swelling the applied latex material, in order to be rolled off in another process stage by means of a stripping device 5 and to be then stored in a collecting basket not shown.

Three brush units are present in a further brush device 6, which, on the one hand, assure that no prophylactics or other residues remain hanging on the immersion tools, and which, on the other hand, produce a cleaning effect.

After the immersion tools 14 have been brushed clean in the brush device 6, they are directly admitted into the first immersion bath 7, which is filled with latex mixture. It is important in this connection that the immersion tools 14 have a certain temperature, which has been found to be the mean value across the entire length of the conveyor belt in the individual treatment stages. Prior to the first immersion stage in the immersion tub 7, it has to be assured that the surface of the immersion tools 14 is not completely dry, but has a low content of moisture. In the first immersion tub of the exemplified embodiment described here, the respective immersion tool 14 is immersed about 100 mm in the immersion bath only with its contoured part 17. Due to a rail 7a according to the invention, which is arranged above the immersion tub 7, the immersion tool 14 is, on the one hand, forced from its vertical position into a slanted position, and the immersion tool is, on the other hand, put into rotation by friction grip. The rotation of the immersion tool 14 continues throughout the entire immersion process. For a short time, the immersion tool 14 passes through the latex bath with the preset length of immersion, and is then gradually guided from the bath. The immersion depth in the first immersion tub 7 is obtained in the first so-called point immersion by setting the entire immersion tub 7 lower as a whole. The immersion tools 14 are immersed in the slanted position, and the suspended immersion tools 14 emerge vertically to the surface of the immersion bath in the standing position. In the first so-called point immersion, the immersion tools 14 immerse in the latex bath slightly later, and emerge again from the latex bath about 1 m before the end of the immersion tub 7.

So that a direct drying phase can start following the point immersion, the drying device 8 is mounted advanced about 1 m above the latex immersion tub 7, so that the wetted immersion tools 14 can drive in the horizontal position into the first drying furnace 8. Drying in said drying device 8 only relates to the wetted tip of the immersion tool 14, whereby the heat is directed in such a way that only the tip of the tool is heated.

Immediately following completion of the drying process, i.e., as soon as the immersion tool 14 has left the surface of the liquid material, the immersion tool 14 is put into rotation by a mechanism mounted on the open end of the immersion tool and turned at the same time by 90° into the horizontal position. In said horizontal position, the immersion tool 14 wetted with elastic material passes through the first drying stage in the drying furnace 8. Said drying furnace 8 is operated with a defined temperature profile, the maximum temperature of which does not exceed about 70°. During said first drying stage in the drying furnace 8, the elastic material (latex) applied to the tool 14 is subjected to a certain curing or fastening and, on the other hand, prepared for the second immersion process in the second immersion tub 9, and water residues, if any, are removed by evaporizing.

The surface of the tool 14 coated after the first immersion process in the front part 17 of the immersion tool 14 is now prepared in such a way that a second immersion step can follow, in which the immersion tool 14 is immersed up to the end of the actual length of the prophylactic reduced by the material consumption for forming a rolling ring 20. The immersion takes place relatively quickly as compared to the re-emergence. Immediately after the immersion tool 14 has left the surface of the immersion bath (latex), it is put into rotation again and brought into a horizontal position, in which it passes through the second drying stage in the furnace 10. The drying furnace 10 is operated with a defined temperature profile as well, with the maximum temperature of such profile amounting to about 70° C. The pass-through speed is determined by the conveying speed of the endless conveyor belt 3 and it is constant during a production cycle. The dwelling time, therefore, depends on the length of the respective drying furnace.

After the immersion tool has left on the endless conveyor belt 3 the drying furnace 10, the third and last drying stage takes place in the immersion tub 11. In said immersion tub 11, the immersion tool 14 immerses in the same way as described before in the immersion tub 11 up to a length barely below the length of immersion in the preceding immersion stage in the immersion tub 9. Following the third and last immersion stage in the immersion tub 11, a drying takes place again in the drying furnace 13, such drying taking place in a similar way as described before. subsequently, the formation of a rolling ring 20 (FIG. 4) takes place, which is formed with the help of rotating brushes not shown here in detail. Following the manufacture of the rolling ring 20 on the immersion tool 14 in the device 13a, the immersion tool passes through another drying stage 13b.

Following the manufacture of the rolling ring 20 on the immersion tool 14, the immersion tool with the already finished prophylactic passes through the last heat treatment in the heating furnace 12, in which a drying process starts first.

The furnace 12, which extends across the entire length of the device on the top part of the endless conveyor belt 3, is operated with a highly defined temperature program and a defined temperature profile, whereby the maximum temperature within the furnace 12 does not exceed 110° C. The dwelling time of the finished prophylactic, of course, depends again on the speed of the endless conveyor belt 3 and typically comes to between 6 cm/s and 8 cm/s, from which results a dwelling time of about 9 minutes. After leaving the furnace 12, the finished prophylactic on the immersion tool 14 is immersed via the reversing wheel 2 in the aforementioned liquor bath 4 in order to cause of swelling of the finished prophylactic.

Figure 2:
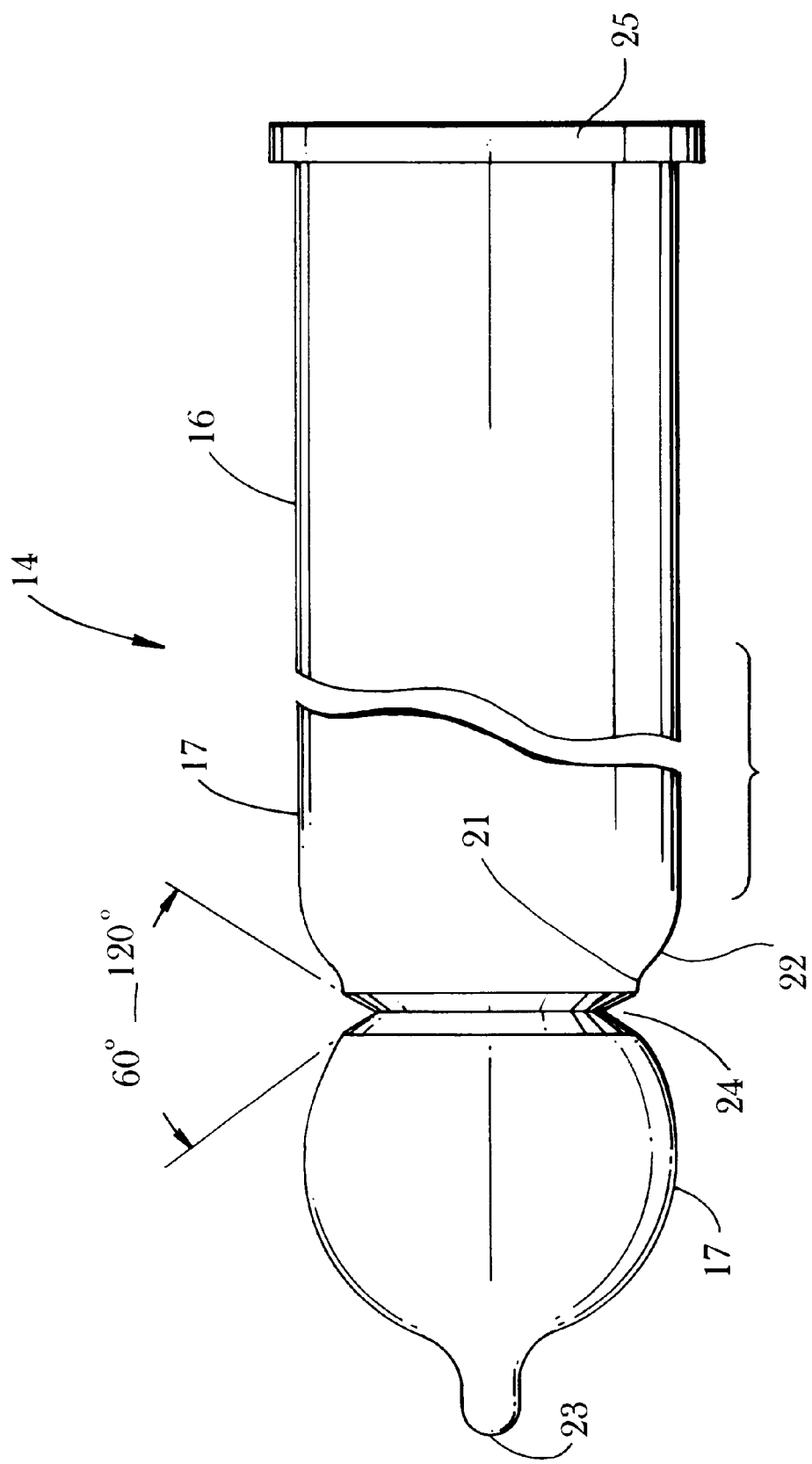
FIG. 2 shows a lateral view of an immersion tool (14) according to the invention, which is made of glass.

The immersion tool 14 is shown in FIG. 2 by a lateral view. In this case, the immersion tool 14 consists of a long-stretched glass cylinder (350 mm long), which is substantially subdivided in the two zones 16 and 17, whereby the zone 16 is a long-stretched, straight cylinder, which is adjoined in this representation on the left side by a shaped part 17, which is closed at the end. On the open part 16 of the glass cylinder, a step 25 is present, which serves the purpose of fastening the entire immersion tool 14 on a holding device—not explained in greater detail—on the endless conveyor belt 3. At its left end, the shaped part 17 of the immersion tool 14 has a bulging, which is about 15 mm long and has a diameter of about 15 mm at its left end. On the later, finished prophylactic, the so-called reservoir is produced by said bulging. The transition from the bulging 23 to the widened front part 17 takes place with a suitably softly extending radius of curvature. The widened front part 17 of the immersion tool 14, furthermore, has a cylindrical, straight part, which is about 15 mm long.

The straight part is followed by a deepening 22, which practically represents a constriction of the diameter of the immersion tool 14. About in the center of the deepening 22, a straight piece extends across a short range, such piece being about 6 mm long. In the center of said straight deepening extending parallel with the longitudinal axis, an annular groove 24 is present, which is essential to the invention, with its opening angle varying between 60° and 120°. The depth of the annular groove 24 depends on the needs of the user of the prophylactic and is between 0.3 and 1.5 mm. The cross sectional form of the annular groove 24 is not fixed a priori but dependent on the elastic material to be used. For example, an annular groove having a triangular cross section can be selected, which may have relatively small radii of curvature at the points of transition to the flat part of the deepening 22 (see FIG. 2). Another conceivable annular groove 24 is shown in FIG. 3. Here, the transitions from the flat parts extend with a relatively large radius of curvature, whereby, however, the opening angle remains the same between 60° and 120°.

The annular groove 24 is worked in with known means used in the trade, which are not described here in detail. The same applies to the manufacture of the entire immersion tool 14 made of glass.

FIG. 4 shows a part cutout of the immersion tool 14, to which the two layers 26, 27 of elastic material (latex) are applied first in the individual immersion baths, and on which a rolling ring was subsequently rolled on with the help of rotating brushes. The rotating brushes first engage the first layer 26 and roll the latter together with the second layer 27 to form a rolling ring 20. During the subsequent heat treatment, the rolling ring is interlaced with its individual layers 26 and 27, so that it forms a compact unit.

Figure 5:
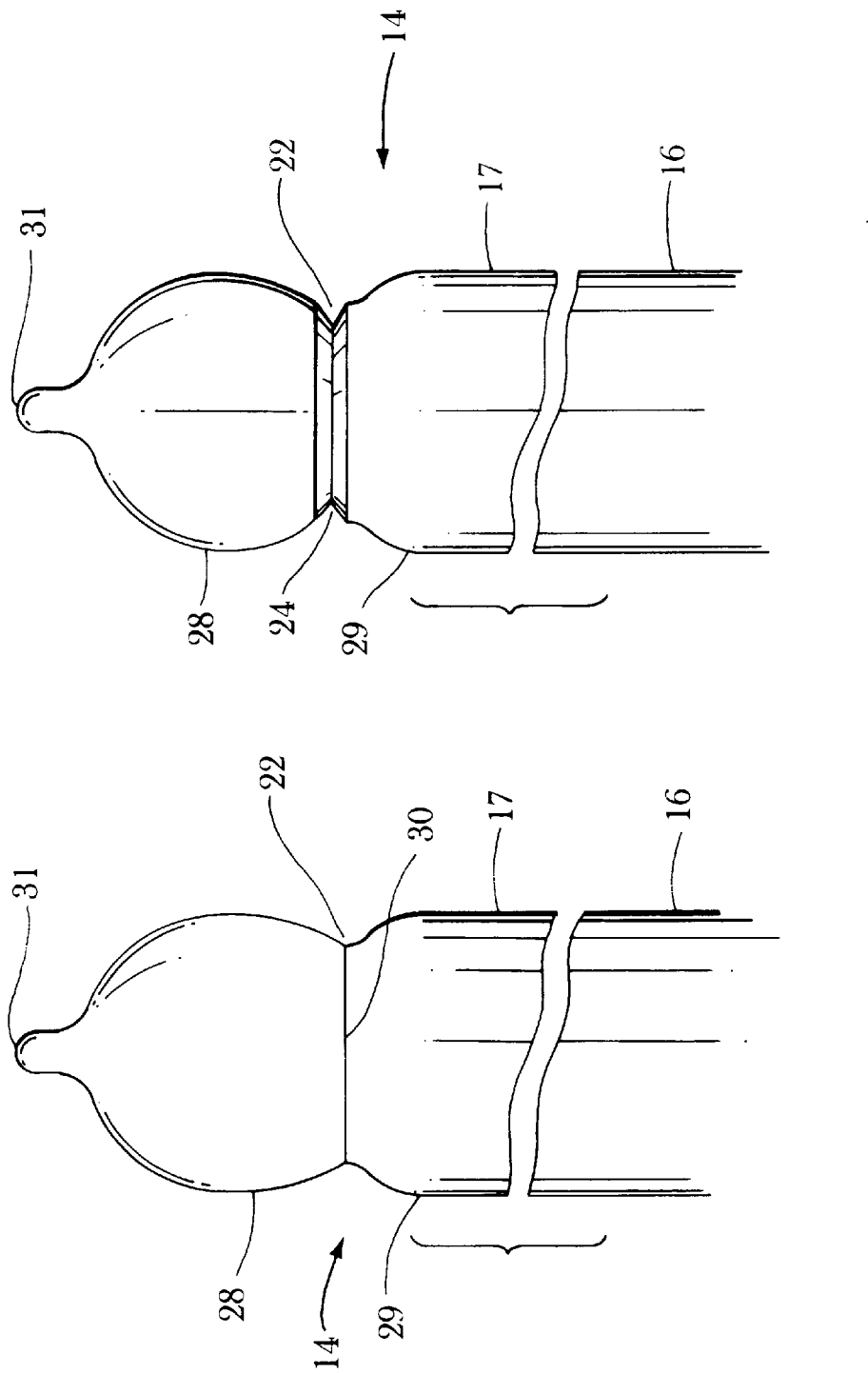
FIG. 5 shows two lateral views of another immersion tool (14) according to the invention, which is made of glass.
Figure 6:
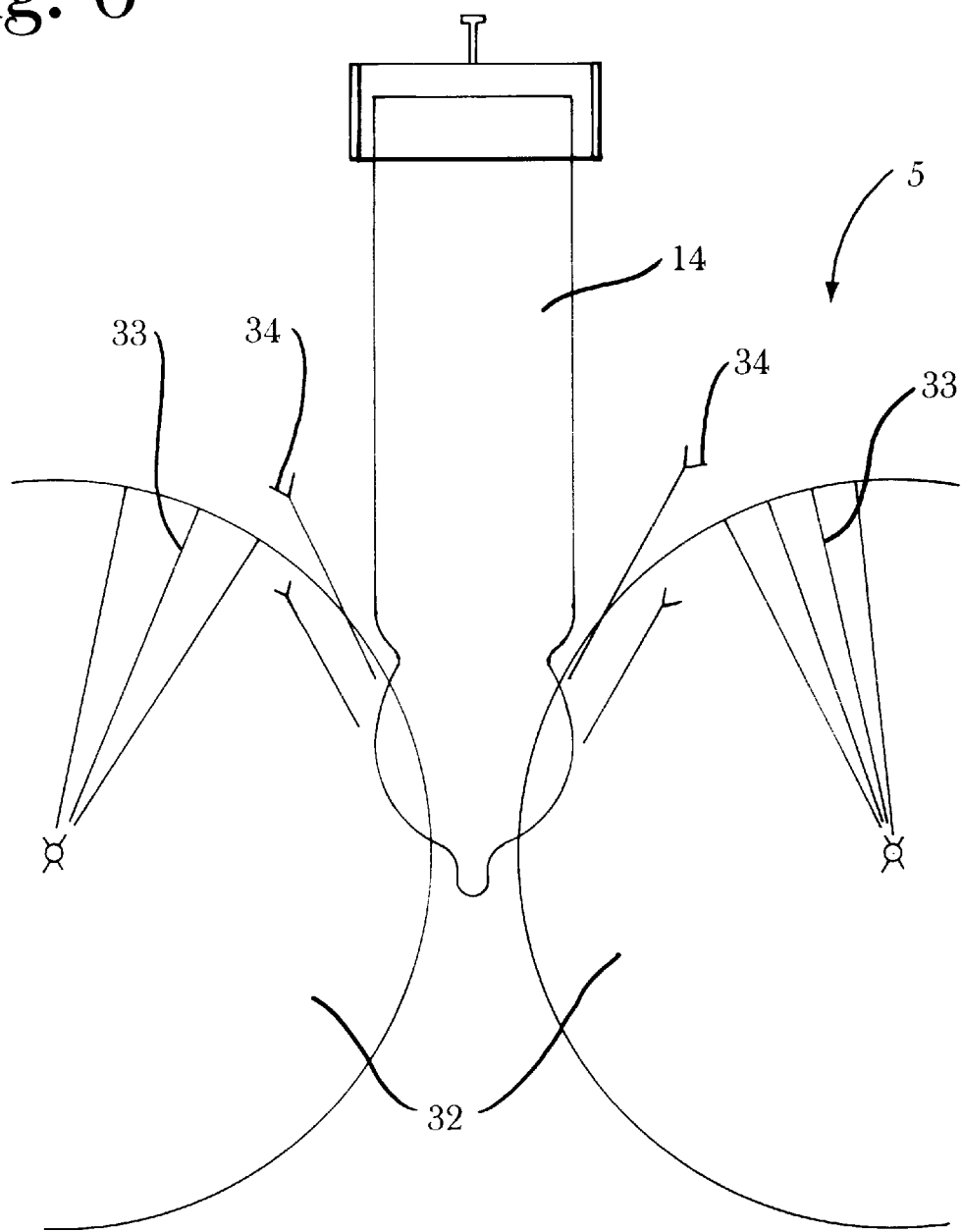
FIG. 6 shows the immersion tool (14) with the schematized stripping device (5).

FIG. 5 shows another exemplified embodiment of the immersion tool 14 according to the invention. The immersion tool 14 consists of a long-stretched, cylindrical part 16, which is adjoined by a contoured part 17 of the immersion tool 14.

This particularly important embodiment of the immersion tool 14 or of the finished prophylactic has its special feature in the fact that on the one hand, the deepening 22 is formed by the two truncated cone-like parts 28 and 29. At the deepest point, where the two small cover surfaces of the truncated cones abut each other, it is possible to selectively work in an annular groove 24 as described above, or the annular groove can be omitted. In case the annular groove is not worked in, it is extremely important that the joint abutments of the truncated cones 28 and 29 form a sharp, pronounced bend 30. With suitable material, such a pronounced bend or groove 30 can cause the formation of the ring according to the invention, it it may replace the annular groove 24 according to the invention. Another important feature of said embodiment according to the invention is the amount of crown of the jacket surfaces of the truncated cones 28 and 29. The diameter of the small cover surfaces of the truncated cones 28, 29 is to be selected between 16 and 30 mm.

According to the present invention, a so-called reservoir 31 is present at the top end of the tool 14, which reservoir, according to the invention, is designed in the present embodiment in the form of a club. It is necessary in this connection to particularly stress the measurements of the reservoir 31, which are between 4 and 10 mm at the lower narrow end, and which amount to 12 mm at the top end. The length of the reservoir 31 comes to about 6 mm.

Due to the contoured form of the immersion tool 14, considerable problems are faced when stripping off the finished prophylactic with the stripping device 5. Said problems are overcome by means of a stripping device 5 according to the invention. Said stripping device 5 according to the invention has the rotating brushes 32, which substantially in opposite directions. During the rotation, the bristles 33 of said brushes touch the surface of the immersion tool 14 and, in this way, cause the prophylactic to be stripped off. However, the stripping process is without problems only in the long-stretched, oblong part of the immersion tool 14, whereas difficulties are faced during stripping in the contoured part of the immersion tool. To overcome these difficulties, one or a plurality of nozzles 34 are arranged laterally of the immersion tool 14 above the brushes 32, which nozzles direct a pressurized water jet in the direction of the contoured part of the immersion tool 14. This results in a trouble-free stripping from the contoured part of the immersion tool 14.

I claim:

1. A device for producing a thin-walled prophylactic, which comprises
    (a) an endless conveyor belt having a length,
    (b) an immersion tool mounted on the belt consisting of
        (i) a cylindrical section and
        (ii) a shaped section, having an annular groove and a reservoir part;
        the immersion tool being closed at one end and having on its surface a certain contour with a deepening starting about 50 mm from the closed end and extending across about 30 mm;
    (c) three immersion tubs, in which a latex mixture substantially consisting of natural rubber is present, the first of the three immersion tubs being deeper relative to the endless conveyor belt than the other two immersion tubs;
    (d) a first drying furnace arranged between the first and the second immersion tubs, a second drying furnace arranged between the second and the third immersion tubs, the furnaces being operated with a defined temperature profile and temperature program in which the maximum temperature amounts to about 70 degrees C.;
    (e) a third drying furnace, a brush device and a fourth drying furnace following the third immersion tub;
    (f) a fifth furnace extending across the length of the endless conveyor belt, said fifth furnace being operated with a defined temperature profile and temperature program, whereby the maximum temperature does not exceed about 110 degrees C.;
    (g) a rail extending along the first immersion tub, said rail providing the longitudinal axis of the immersion tool with a certain slanted position and putting the immersion tool into rotation; and
    (h) a stripping device having brushes rotating in opposite directions, and a pressurized water jet acting on a front part of the immersion tool.

2. A device according to claim 1 wherein the deepening has a center, and in the center, a straight part.

3. A device according to claim 2 wherein the annular groove is present in about the center of the straight part, with the opening angle of said grooves varying between 60 degrees and 120 degrees.

4. A device according to claim 1 wherein the annular groove has no sharp points, corners and edges.

5. A device according to claim 3 wherein the depth of the annular groove varies between 0.3 and 1.5 mm.

6. A device according to claim 1 wherein the deepening is composed of two approximately identical, conical, truncated parts having small cover surfaces, the small cover surfaces of the truncated cones abutting each other to form a sharp separation line.

7. A device according to claim 6 wherein the separation line has an annular groove.

8. A device according to claim 6 wherein the truncated cones have spherical jacket surfaces.

9. A device according to claim 6 wherein the diameter of the separation line varies between 16 and 30 mm.

10. A device according to claim 1 wherein the immersion tool comprises an elongated glass cylinder, and the reservoir part has an upper portion and a lower portion narrower than the upper portion, the upper portion being formed in the shape of a club, and the lower portion adjoining the glass cylinder, the diameter of the lower portion varying between 4 and 10 mm.

11. A device according to claim 1 wherein the immersion tool comprises an elongated glass cylinder, and the reservoir part has an upper portion and a lower portion narrower than the upper portion, the upper portion being formed in the shape of a club, and the lower portion adjoining the glass cylinder, the diameter of the upper portion being 12 mm and length of the reservoir being 16 mm.

12. A device for producing a thin-walled prophylactic, which comprises (a) an endless conveyor belt having a length, (b) an elongated glass tool mounted on the belt consisting of (i) a cylindrical section and
      (ii) a shaped section, having an annular groove and a reservoir part;

the immersion tool being closed at one end and having on its surface a certain contour with a deepening starting about 40 mm from the closed end and extending across about 60 mm;

(c) three immersion tubs, in which a latex mixture substantially consisting of natural rubber is present, the first of the three immersion tubs being disposed substantially deeper relative to the endless conveyor belt than the other two immersion tubs;

(d) a first drying furnace arranged between the first and the second immersion tubs, a second drying furnace arranged between the second and the third immersion tubs, the furnaces being operated with a defined temperature profile and temperature program in which the maximum temperature amounts to about 70 degrees C.;

(e) a third drying furnace, a brush device and a fourth drying furnace following the third immersion tub;

(f) a fifth furnace extending across the length of the endless conveyor belt, said fifth furnace being operated with a defined temperature profile and temperature program, whereby the maximum temperature does not exceed about 110 degrees C.;

(g) a rail extending along the first immersion tub, said rail providing the longitudinal axis of the immersion tool with a certain slanted position and putting the immersion tool into rotation; and (h) a stripping device having brushes rotating in opposite directions, and a pressurized water jet acting on a front part of the immersion tool.

* * * * *